United States Patent
Sakaguchi

(10) Patent No.: US 12,350,095 B2
(45) Date of Patent: Jul. 8, 2025

(54) DIAGNOSTIC IMAGING CATHETER AND DIAGNOSTIC IMAGING APPARATUS

(71) Applicant: TERUMO KABUSHIKI KAISHA, Tokyo (JP)

(72) Inventor: Yuki Sakaguchi, Isehara (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 775 days.

(21) Appl. No.: 17/377,982

(22) Filed: Jul. 16, 2021

(65) Prior Publication Data

US 2021/0338199 A1 Nov. 4, 2021

Related U.S. Application Data

(63) Continuation of application No. PCT/JP2020/001609, filed on Jan. 17, 2020.

(30) Foreign Application Priority Data

Jan. 17, 2019 (JP) ................................. 2019-006437

(51) Int. Cl.
*A61B 8/12* (2006.01)
*A61B 5/00* (2006.01)
(Continued)

(52) U.S. Cl.
CPC .............. *A61B 8/12* (2013.01); *A61B 5/0084* (2013.01); *A61M 25/003* (2013.01); *A61M 25/0662* (2013.01); *A61M 39/14* (2013.01)

(58) Field of Classification Search
CPC ....... A61B 8/12; A61B 5/0084; A61B 1/0016; A61B 1/3137; A61B 1/05; A61B 1/0676;
(Continued)

(56) References Cited

U.S. PATENT DOCUMENTS

2012/0271174 A1 10/2012 Iwahashi
2016/0354111 A1 12/2016 Miyagawa et al.
(Continued)

FOREIGN PATENT DOCUMENTS

CN 106413592 A 2/2017
JP H10272137 A 10/1998
(Continued)

OTHER PUBLICATIONS

International Search Report (PCT/ISA/210) with translation and Written Opinion (PCT/ISA/237) mailed on Mar. 24, 2020, by the Japanese Patent Office as the International Searching Authority for International Application No. PCT/JP2020/001609.
(Continued)

*Primary Examiner* — Oommen Jacob
*Assistant Examiner* — Steven Maldonado
(74) *Attorney, Agent, or Firm* — BUCHANAN INGERSOLL & ROONEY PC

(57) ABSTRACT

A diagnostic imaging catheter includes: a drive shaft including a signal transmitter and receiver at a distal end portion and configured to rotate and move forward and backward; a support tube on an outer periphery of the drive shaft along an axial direction and configured to move forward and backward i with the drive shaft; a sheath in which the drive shaft is positioned; a relay connector connected to a proximal end of the sheath; and a sealing member providing a seal between the relay connector and the support tube at a position proximal of the sheath proximal end. The relay connector includes a main lumen extending from the sealing member to the sheath proximal end and an injection lumen communicating with the main lumen at a communication port. A distal end of the support tube is movable to a position proximal of the front edge of the communication port.

18 Claims, 6 Drawing Sheets

(51) Int. Cl.
*A61M 25/00* (2006.01)
*A61M 25/06* (2006.01)
*A61M 39/14* (2006.01)

(58) Field of Classification Search
CPC ............ A61B 2562/225; A61B 5/0062; A61B 5/6855; A61B 5/6876; A61B 8/445; A61M 25/003; A61M 25/0662; A61M 39/14
See application file for complete search history.

(56) References Cited

U.S. PATENT DOCUMENTS

| | | | | |
|---|---|---|---|---|
| 2016/0374710 | A1* | 12/2016 | Sinelnikov | A61B 17/3207 600/439 |
| 2017/0055941 | A1* | 3/2017 | Stigall | A61B 8/12 |
| 2017/0079617 | A1* | 3/2017 | Yamamoto | A61B 6/12 |
| 2017/0333001 | A1* | 11/2017 | Sakaguchi | A61B 8/461 |

FOREIGN PATENT DOCUMENTS

| | | | | |
|---|---|---|---|---|
| JP | 3000503 A1 | * | 3/2016 | ............... A61B 8/12 |
| JP | WO 2017047330 A1 | * | 3/2017 | ......... A61B 1/00071 |
| JP | WO 2017164071 A1 | * | 9/2017 | ............... A61B 8/12 |
| JP | 2017205430 A | | 11/2017 | |

OTHER PUBLICATIONS

Office Action (The First Office Action) issued Mar. 1, 2023, by the National Intellectual Property Administration, P. R. China in corresponding Chinese Patent Application No. 202080009147.0 and an English translation of the Office Action. (13 pages).

English Translations of the International Search Report (Form PCT/ISA/210) and the Written Opinion of the International Searching Authority (Form PCT/ISA/237) issued on Mar. 24, 2020, by the Japanese Patent Office in corresponding International Application No. PCT/JP2020/001609. (8 pages).

* cited by examiner

DIAGNOSTIC IMAGING CATHETER AND DIAGNOSTIC IMAGING APPARATUS

This application is a continuation of International Patent Application No. PCT/JP2020/001609 filed on Jan. 17, 2020, which claims priority to Japanese Patent Application No. 2019-006437 filed on Jan. 17, 2019, the entire content of both of which is incorporated herein by reference.

FIELD OF THE INVENTION

The present disclosure generally relates to a diagnostic imaging catheter and a diagnostic imaging apparatus.

BACKGROUND DISCUSSION

A diagnostic imaging catheter including a drive shaft provided with a signal transmitter and receiver at a distal end portion and capable of rotating and moving forward and backward, and a sheath into which the drive shaft is inserted is known. The diagnostic imaging catheter requires priming processing in which a lumen of the sheath is filled with a priming liquid such as physiological saline prior to use for the purpose of smoothly transmitting and receiving signals such as ultrasounds.

For example, Japanese Patent Application Publication No. 2017-205430 describes a diagnostic imaging catheter that enables easy priming processing by reducing a flow path resistance of a priming liquid by providing an injection port for the priming liquid in a relay connector connected to a base end of a sheath. The diagnostic imaging catheter includes a support tube provided on an outer periphery of a drive shaft along an axial direction and moving forward and backward in conjunction with the drive shaft. The relay connector is divided into a main lumen that extends from a sealing member that seals between the relay connector and the support tube to the base end of the sheath and an injection lumen that communicates with the main lumen at a communication port and can inject the priming liquid.

The diagnostic imaging catheter described in Japanese Patent Application Publication No. 2017-205430 is configured such that even when the drive shaft and the support tube are pulled most toward the base end, a distal end of the support tube is located in front of a front end of the communication port. Therefore, there is room for such a diagnostic imaging catheter to further reduce the flow path resistance of the priming liquid.

SUMMARY

The diagnostic imaging catheter and diagnostic imaging apparatus disclosed here is configured to reduce a flow path resistance of a priming liquid and enabling smooth priming processing.

A diagnostic imaging catheter as a first aspect of the disclosure comprises: an axially extending drive shaft that includes a distal end portion, and a signal transmitter and receiver at the distal end portion of the drive shaft. The drive shaft and the signal transmitter and receiver are rotatable together and being movable together axially forward and backward. A support tube is provided on an outer periphery of the drive shaft and extends in an axial direction along a part of an axial extent of the drive shaft, with the support tube being configured to move axially forward and backward together with the drive shaft. The diagnostic imaging catheter also includes a sheath in which the drive shaft is positioned, a relay connector connected to the proximal end of the sheath, and a sealing member positioned to provide a seal between the relay connector and the support tube at a position proximal of the proximal end of the sheath. The relay connector is divided into a main lumen that extends from the sealing member to the proximal end of the sheath and an injection lumen into which is injectable a priming liquid, with the injection lumen communicating with the main lumen at a communication port so that the priming liquid injected into the injection port flows into the main lumen by way of the communication port. The support tube is axially movable so that the distal end of the support tube is positionable proximal of a distal end of the communication port.

In one embodiment, the distal end of the support tube is movable to a position in front of the front end of the communication port.

The distal end of the support tube is located in front of the front end of the communication port at the end of a pullback operation by an external device.

In one embodiment, the distal end of the main lumen of the relay connector and the proximal end of a lumen of the sheath are flush with each other.

A diagnostic imaging apparatus as a second aspect of the disclosure includes: a diagnostic imaging catheter; and an external device to which the diagnostic imaging catheter is connectable. The diagnostic imaging catheter includes an axially extending drive shaft, a support tube, a sheath, a relay connector and a sealing member. The drive shaft includes a distal end portion at which is located a signal transmitter and receiver, with the drive shaft and the signal transmitter and receiver being rotatable together and being movable together axially forward and backward. The support tube is provided on an outer periphery of the drive shaft and extends in an axial direction along a part of an axial extent of the drive shaft, with the support tube being configured to move axially forward and backward together with the drive shaft. The drive shaft is positioned in the sheath, and the relay connector is connected to the proximal end of the sheath. The sealing member provides a seal between the relay connector and the support tube at a position proximal of the proximal end of the sheath. The relay connector is divided into a main lumen that extends from the sealing member to the proximal end of the sheath and an injection lumen into which is injectable a priming liquid. The injection lumen communicates with the main lumen at a communication port so that the priming liquid injected into the injection port flows into the main lumen by way of the communication port, the communication port including a distal end. The support tube is axially movable so that the distal end of the support tube is positionable proximal of a distal end of the communication port. The external device includes a limiting portion that limits axial backward movement of the distal end of the support tube of the diagnostic imaging catheter when the diagnostic imaging catheter is connected to the external device and the external device is performing a pullback operation of the drive shaft so that the distal end of the support tube does not move proximally beyond the distal end of the communication port.

According to the present disclosure, it is possible to provide a diagnostic imaging catheter and a diagnostic imaging apparatus capable of reducing a flow path resistance of a priming liquid and enabling smooth priming processing.

In accordance with another aspect, a method comprises positioning the distal end of a diagnostic imaging catheter in a blood vessel. The diagnostic imaging catheter comprises: an axially extending drive shaft that includes a signal transmitter and receiver at a distal end portion of the drive shaft, with the drive shaft and the signal transmitter and receiver being movable together axially forward and backward; a support tube surrounding an outer periphery of the drive shaft and extending in an axial direction along a part of an axial extent of the drive shaft, with the support tube movable axially forward and backward together with the drive shaft; a sheath having a lumen in which the drive shaft is positioned; a relay connector connected to the proximal end of the sheath; a sealing member providing a seal between an inner surface of the relay connector and an outer surface of the support tube, with the sealing member being located proximal of the proximal end of the sheath; and the relay connector including a main lumen and an injection lumen, with the main lumen extending from the sealing member to the proximal end of the sheath, and the injection lumen communicating with the main lumen at a communication port so that the priming liquid in the injection port flows into the main lumen by way of the communication port, the communication port including a distal end; and wherein the support tube is axially movable so that the distal end of the support tube is positionable proximal of a distal end of the communication port. The method additionally comprises introducing priming liquid into the injection lumen so that the priming liquid flows into the main lumen by way of the communication port and flows from the main lumen into the lumen in the sheath, wherein the priming liquid flows into the main lumen by way of the communication port while a distal end of the support tube is positioned proximal of a distal edge of the communication port. The method also includes operating an external device connected to the diagnostic imaging catheter to perform a pullback operation in which the drive shaft is rotated and moved axially backward, wherein the distal end of the support tube is distal of the distal edge of the communication port at an end of the pullback operation.

DETAILED DESCRIPTION

Set forth below with reference to the accompanying drawings is a detailed description of an embodiment of a diagnostic imaging catheter and a diagnostic imaging apparatus representing examples of the inventive diagnostic imaging catheter and diagnostic imaging apparatus disclosed here.

Figure 1:
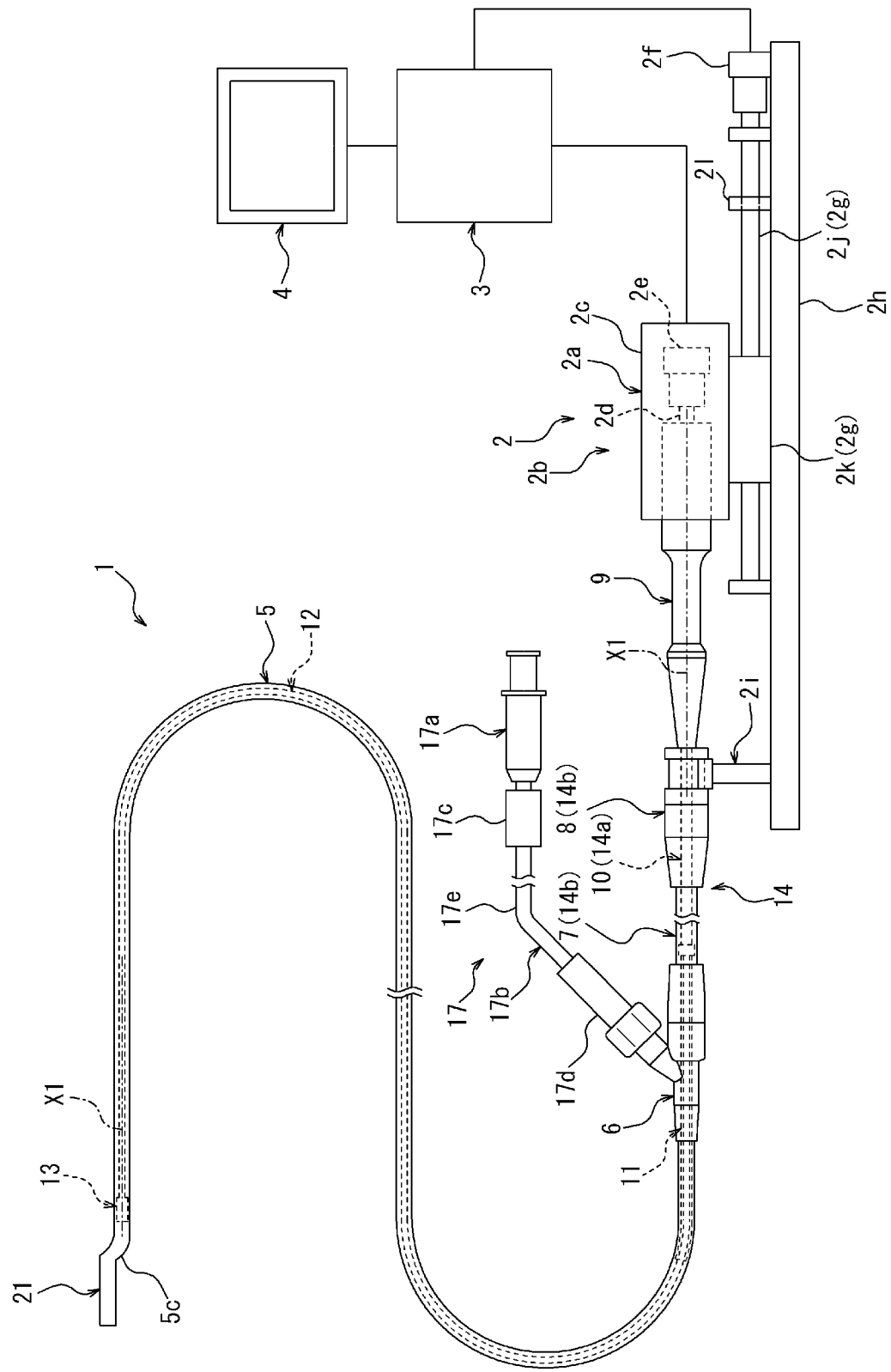
FIG. 1 is an external view showing a state immediately before a pullback operation of a diagnostic imaging catheter by an external device according to an embodiment of the invention.

As shown in FIG. 1, a diagnostic imaging catheter 1 (hereinafter, also referred to as a catheter 1) according to the present embodiment can be used together with an external device 2, a control device 3, and a display 4 to image the inside of a vessel such as a blood vessel in a living body such as a human body and display the image. That is, the catheter 1, the external device 2, the control device 3, and the display 4 form the diagnostic imaging apparatus. The diagnostic imaging apparatus including the catheter 1 and the external device 2 may be configured by integrating the control device 3 and the display 4 with the external device 2. The catheter 1 includes a sheath 5, a relay connector 6, an outer tube 7, a unit connector 8, a hub 9, an inner tube 10, a support tube 11, and a drive shaft 12.

A distal end portion of the relay connector 6 is integrally connected to a base end portion of the sheath 5. A distal end portion of the outer tube 7 is integrally connected to a base end portion of the relay connector 6. A distal end portion of the unit connector 8 is integrally connected to a base end portion of the outer tube 7.

A base end portion of the inner tube 10 is integrally connected to a distal end portion of the hub 9. A base end portion of the support tube 11 is integrally connected to a distal end portion of the inner tube 10.

The drive shaft 12 has a long (elongated) shape having a central axis X1. A base end portion of the drive shaft 12 is rotatably pivotally supported by the hub 9 around the central axis X1. The drive shaft 12 has a signal transmitter and receiver 13 at a distal end portion. The signal transmitter and receiver 13 can transmit a signal (inspection waves) such as an ultrasound signal or an optical signal to the vessel (e.g., blood vessel) and receive a reflected signal. Inside the drive shaft 12, a signal line that enables communication between the signal transmitter and receiver 13 and the control device 3 via the external device 2 is provided. The signal transmitter and receiver 13 can rotate around the central axis X1 integrally with the drive shaft 12.

The drive shaft 12 is inserted into or positioned in the sheath 5, the relay connector 6, the outer tube 7, the unit connector 8, the support tube 11, the inner tube 10, and the hub 9.

Figure 2:
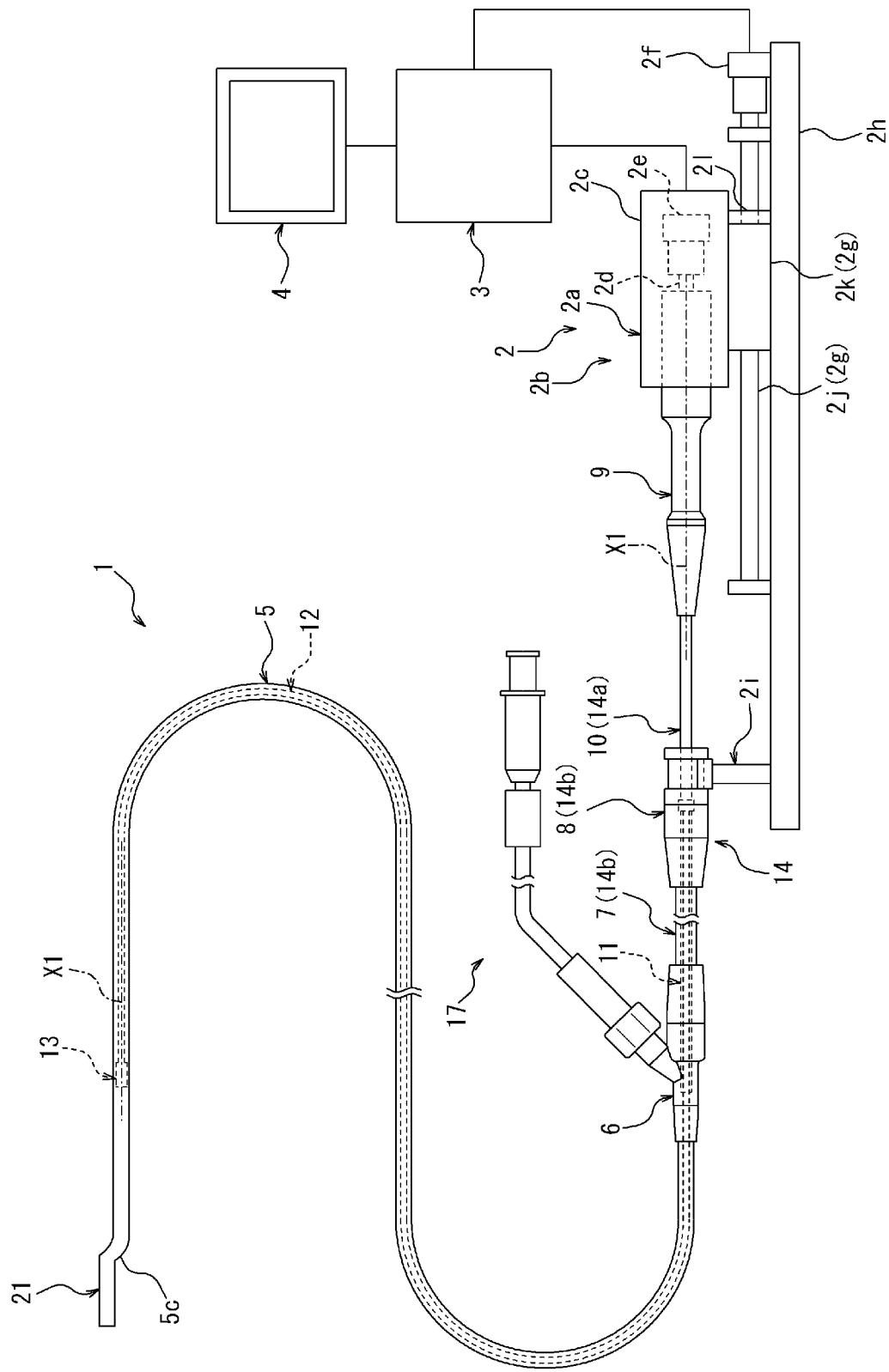
FIG. 2 is an external view showing a state at the end of the pullback operation started from the state shown in FIG. 1.

As shown in FIGS. 1 and 2, the hub 9, the inner tube 10, the support tube 11, and the drive shaft 12 can move forward and backward integrally (that is, can move forward and can move backward) with respect to the sheath 5, the relay connector 6, the outer tube 7, and the unit connector 8. Forward movement means movement from a base end side to a distal end side, and backward movement means movement in an opposite direction (i.e., a direction from the distal end side to the base end side). Forward is a direction from the base end side to the distal end side, and backward is an opposite direction (i.e., in a direction from the base end side to the distal end side).

The inner tube 10 together with the relay connector 6 and the outer tube 7 form a telescope portion 14. The telescope portion 14 includes an inner cylinder 14a formed of the inner tube 10 and an outer cylinder 14b formed of the relay connector 6 and the outer tube 7. The telescope portion 14 can be expanded and contracted by moving the inner cylinder 14a forward and backward inside the outer cylinder 14b.

Figure 5:
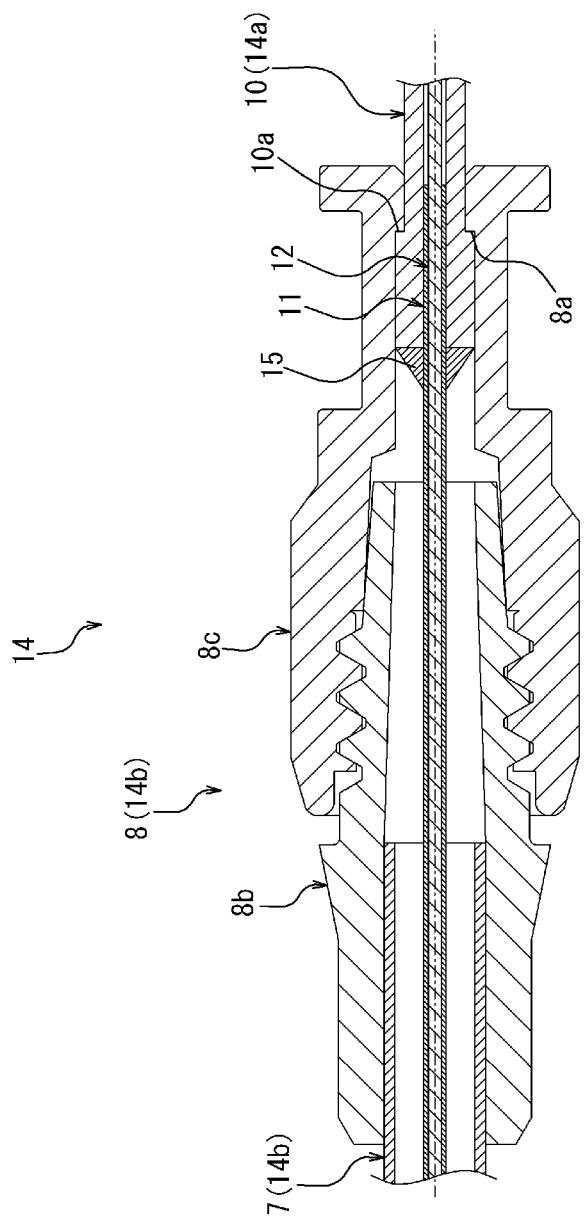
FIG. 5 is a cross-sectional view showing a peripheral portion of a unit connector in a state where a drive shaft and a support tube are in a backward limit position.

The telescope portion 14 can be expanded and contracted between a contraction limit state in which further contraction is regulated and an expansion limit state in which further expansion is regulated. As shown in FIG. 1, the telescope portion 14 is configured to be in the contraction limit state when a distal end surface of the hub 9 comes into contact with a base end surface of the unit connector 8. The telescope portion 14 may be configured to be in the contraction limit state due to contact between other surfaces. As shown in FIG. 5, the telescope portion 14 is configured to be in the expansion limit state when a stepped surface 10a provided at the distal end portion of the inner tube 10 comes into contact with a stepped surface 8a provided inside the unit connector 8. The stepped surface 10a of the inner tube 10 and the stepped surface 8a of the unit connector 8 each have an annular shape whose diameter increases from the base end side to the distal end side. The telescope portion 14 may be configured to be in the expansion limit state due to contact between other surfaces.

The hub 9, the inner tube 10, the support tube 11, and the drive shaft 12 can move forward and backward between a forward limit position (see FIG. 1) in which the telescope portion 14 is in the contraction limit state and a backward limit position (see FIG. 5) in which the telescope portion 14 is in the expansion limit state.

As shown in FIG. 5, the base end portion of the support tube 11 is fixed to a distal end surface of the inner tube 10 by an adhesive 15. The base end portion of the support tube 11 and the distal end portion of the inner tube 10 may be fixed to each other by a fixing method such as welding other than the adhesive 15. The unit connector 8 is formed of a distal end side member 8b having a male threaded portion and a base end side member 8c having a female threaded portion screwed (threadably engaged) with the male threaded portion. However, the number of members forming the unit connector 8 can be increased or decreased as appropriate.

As shown in FIG. 1, the external device 2 includes a rotation drive unit 2a that rotationally drives the drive shaft 12, and a forward and backward movement mechanism 2b that moves the drive shaft 12 forward and backward.

The rotation drive unit 2a includes a housing 2c to which the hub 9 can be attached and detached, and a spindle 2d to which the drive shaft 12 can be attached and detached while being disposed inside the housing 2c. The spindle 2d can connect a communication line inside the drive shaft 12 to the control device 3 in a communicable manner by connecting to the base end portion of the drive shaft 12 via a connector rotatably pivotally supported around the central axis X1 inside the hub 9. Further, the spindle 2d can rotate the drive shaft 12 around the central axis X1 by rotating around the central axis X1 by a rotation drive source 2e such as a motor in a state where the spindle 2d is connected to the drive shaft 12.

The forward and backward movement mechanism 2b includes the housing 2c of the rotation drive unit 2a, a rotation drive source 2f such as a motor, a ball screw mechanism 2g that moves the housing 2c forward and backward by the rotation drive source 2f, a base 2h that supports the ball screw mechanism 2g, and a unit connector fixing portion 2i that is integrally connected to the base 2h. The ball screw mechanism 2g includes a screw shaft 2j that is pivotally supported by the base 2h and is rotationally driven by the rotation drive source 2f, and a nut 2k that is fixed to the housing 2c. The unit connector fixing portion 2i can fix the unit connector 8 by detachably engaging with the unit connector 8.

In a state where the catheter 1 is attached to the external device 2, the external device 2 can perform, based on a control signal from the control device 3, a pullback operation of rotating the drive shaft 12 by the rotation drive unit 2a from a state where the drive shaft 12 is in the forward limit position as shown in FIG. 1 and moving the drive shaft 12 backward to a predetermined position in front of (forward or distal of) the backward limit position as shown in FIG. 2.

A rotation speed of the drive shaft 12 may be, for example, 1800 rpm. The control device 3 may be implemented as a processor such as a CPU.

From the start to the end of the pullback operation, the signal transmitter and receiver 13 transmits a signal (inspection waves) to a vessel (e.g., blood vessel) while the drive shaft 12 is rotated, and receives a reflected signal. The signal transmitter and receiver 13 transmits a measurement signal based on the received signal to the control device 3 through the signal line inside the drive shaft 12. The control device 3 displays an image of the vessel based on the measurement signal on the display 4.

Figure 3:
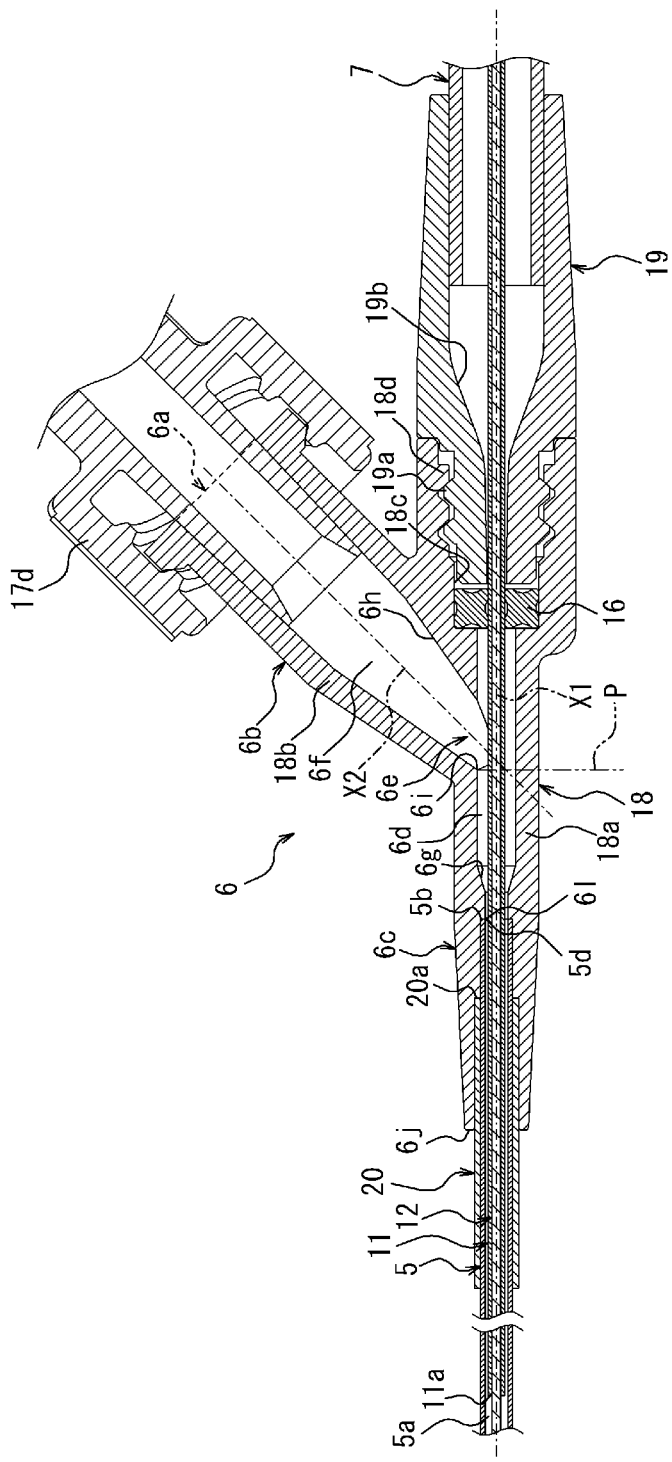
FIG. 3 is a cross-sectional view showing a peripheral portion of a relay connector in the state shown in FIG. 1.

The catheter 1 requires a priming processing in which a lumen 5a of the sheath 5 (see FIG. 3) is filled with a priming liquid such as physiological saline, which is performed prior to imaging the vessel by the pullback operation. Therefore, as shown in FIG. 3, the relay connector 6 includes a side pipe 6b that divides an injection port 6a of the priming liquid at a base end. A distal end of the side pipe 6b is integrally connected to a main pipe 6c into which the drive shaft 12, the support tube 11, and the sheath 5 are inserted or positioned.

Inside the main pipe 6c, a sealing member 16 for sealing between the main pipe 6c and the support tube 11 is disposed behind (proximal of) a base end 5b of the sheath 5. An X ring may be used as the sealing member 16. The sealing member 16 may alternatively be, for example, an O-ring.

The main pipe 6c internally defines a main lumen 6d, which extends from the sealing member 16 to the base end 5b of the sheath 5. The side pipe 6b internally defines an injection lumen 6f that communicates with the main lumen 6d at a communication port 6e and can inject the priming liquid. The communication port 6e is located at a distal end of the injection lumen 6f, and the injection port 6a is located at a base end of the injection lumen 6f.

A priming liquid supply device 17 (see FIG. 1) for supplying the priming liquid is connected to a base end of the side pipe 6b. The priming liquid supply device 17 may include a syringe 17a and a connection tube member 17b. The connection tube member 17b includes a base end side connector 17c connected to a distal end portion of the syringe 17a, a distal end side connector 17d connected to the base end of the side pipe 6b, and a tube 17e extending from the base end side connector 17c to the distal end side connector 17d.

As shown in FIG. 3, the relay connector 6 is formed of a first member 18 and a second member 19. The first member 18 includes a main cylinder 18a that internally defines the main lumen 6d and a side cylinder 18b that internally defines the injection lumen 6f.

An outer peripheral surface of the base end portion of the sheath 5 is fixed to an inner peripheral surface of a distal end portion of the main cylinder 18a by a fixing method such as welding. The base end 5b of the sheath 5 abuts against an annular stepped surface provided on the inner peripheral surface of the distal end portion of the main cylinder 18a. A kink preventing tube 20 is provided along the axial direction on an outer periphery of the base end portion of the sheath 5. The base end 5b of the sheath 5 protrudes from a base end 20a of the kink preventing tube 20 toward the base end side. That is, the base end or proximal end 5b of the sheath 5 extends proximally beyond the proximal end of the kink preventing tube 20. An inner peripheral surface of the kink preventing tube 20 is fixed to the outer peripheral surface of the base end portion of the sheath 5 by a fixing method such as welding. An outer peripheral surface of a base end portion of the kink preventing tube 20 is fixed to the inner peripheral surface of the distal end portion of the main cylinder 18a by a fixing method such as welding.

A distal end 6l of the main lumen 6d and the base end 5d of the lumen 5a of the sheath 5 are flush with each other (that is, the distal end 6l and the base end 5d are smoothly connected). In other words, the distal end 6l of the main lumen 6d terminates at the base end 5d of the lumen 5a of the sheath 5. The distal end portion of the main lumen 6d includes a diameter-reduced portion 6g in which the inner diameter of the main lumen 6d gradually decreases toward the front or in the distal direction. The main lumen 6d has a circular cross-sectional shape having a constant shape and size in the axial direction from the diameter-reduced portion 6g to the sealing member 16.

A base end portion (proximal end portion) of the main cylinder 18a is provided with a diameter-increased inner peripheral surface 18c whose inner diameter is increased in a stepped manner from a base end of the main lumen 6d. The sealing member 16 is disposed at a distal end of the diameter-increased inner peripheral surface 18c. A female threaded portion 18d is provided on the diameter-increased inner peripheral surface 18c on a portion on the base end side (proximal side) of the sealing member 16.

A male threaded portion 19a provided on an outer peripheral surface of a distal end portion of the cylindrical second member 19 is screwed into (threadably engaged with) the female threaded portion 18d. The inner peripheral surface of the second member 19 includes a diameter-reduced portion 19b at which the inner diameter of the second member 19 gradually decreases toward the front (toward the distal direction). The outer peripheral surface of the distal end portion of the outer tube 7 is fixed to a portion of the inner peripheral surface of the second member 19 on a base end side (proximal side) of the diameter-reduced portion 19b by a fixing method such as welding.

The sheath 5 has an elongated cylindrical shape, and the lumen 5a is defined inside the sheath 5. A distal end 5c of the sheath 5 is provided with a distal end wall for defining a discharge port configured to discharge the priming liquid from the lumen 5a. The distal end wall may be integrally molded with the sheath 5, or may be molded separately from the sheath 5 and fixed to the distal end of the sheath 5 by a fixing method such as welding. A cylindrical guided portion 21 into which a guide wire can be inserted is provided at the distal end 5c of the sheath 5.

In order to absorb a manufacturing error in a length of each member and adjust a total length from a distal end of the guided portion 21 to a base end of the unit connector 8 to a specified dimension, a base end portion of the second member 19 and the distal end portion of the outer tube 7 are fixed to each other after relative axial direction positions thereof are adjusted.

The main lumen 6d extends concentrically with the central axis X1. The injection lumen 6f has a central axis X2. The central axis X2 intersects the central axis X1 so as to form an acute angle on a base end side of the central axis X1. The injection lumen 6f has a truncated cone-shaped diameter-reduced portion 6h whose inner diameter is gradually reduced from the base end side (proximal end side) to the distal end side along the central axis X2 up to the communication port 6e. A shape of the diameter-reduced portion 6h is not limited to the truncated cone shape. Also, the injection lumen 6f is not limited to having the diameter-reduced portion 6h, and the central axis X2 may not intersect the central axis X1. As shown in FIG. 3, the communication port 6e at which the injection lumen 6f communicates with the main lumen 6d is positioned intermediate the sealing member 16 and the proximal end 5b of the sheath 5.

The support tube 11 is provided on an outer periphery of the drive shaft 12 along the axial direction, and is configured to move forward and backward in conjunction with (together with) the drive shaft 12. More specifically, the support tube 11 moves forward and backward integrally with the drive shaft 12 as described above.

Figure 4:
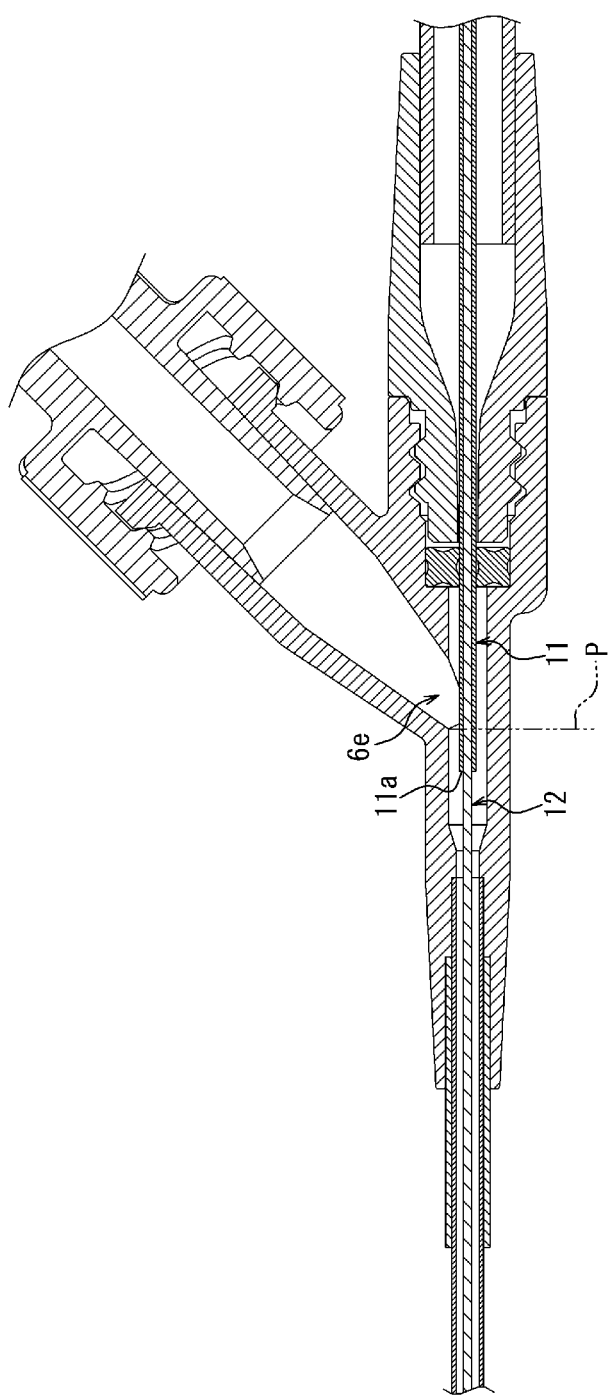
FIG. 4 is a cross-sectional view showing a peripheral portion of the relay connector in the state shown in FIG. 2.

A distal end 11a of the support tube 11 can be moved to a position in front of (distal of) the front end (distal edge) 6i of the communication port 6e. That is, the distal end 11a of the support tube 11 can move to a position in front of the position P at the front end 6i of the communication port 6e in a front-rear direction. Therefore, as shown in FIG. 4, the pullback operation can be performed such that the distal end 11a of the support tube 11 is located in front of (distal of) the position P at the end of the pullback operation by the external device 2. That is, when the pullback operation is completed, the distal end 11a of the support tube 11 can be positioned distal of the position P. More specifically, as shown in FIG. 3, the distal end 11a of the support tube 11 can be moved to a position in front of a distal end 6j of the relay connector 6.

The support tube 11 accommodates the drive shaft 12 with a slight gap allowing smooth rotation of the drive shaft 12 and prevents local deformation of the drive shaft 12. Therefore, the support tube 11 is interposed between the rotating drive shaft 12 and the communication port 6e, and thus it is possible to prevent the occurrence of malfunctions such as the drive shaft 12 being deformed into a twisted shape and entering the communication port 6e and being twisted-off. By controlling the pullback operation such that the distal end 11a of the support tube 11 is located in front of the position P at the end of the pullback operation, it is possible to prevent the occurrence of such a malfunction.

In a state where the catheter 1 is attached to the external device 2, the external device 2 may have a limiting portion 21 (see FIGS. 1 and 2) that limits movement of the support tube so that the distal end of the support tube 11 of the catheter 1 is not moved to a position behind or proximal of the front end 6i of the communication port 6e. With such a limiting portion 21, the occurrence of the above-described malfunctions can be prevented. The limiting portion 21 may be configured such that such a limit can be released.

When the distal end of the support tube 11 is located behind the front end of the communication port 6e, the control device 3 may be configured to perform control such that the rotation drive unit 2a that rotationally drives the drive shaft 12 is not driven. With such a configuration of the control device 3, the occurrence of the above-described malfunctions can be prevented.

Figure 6:
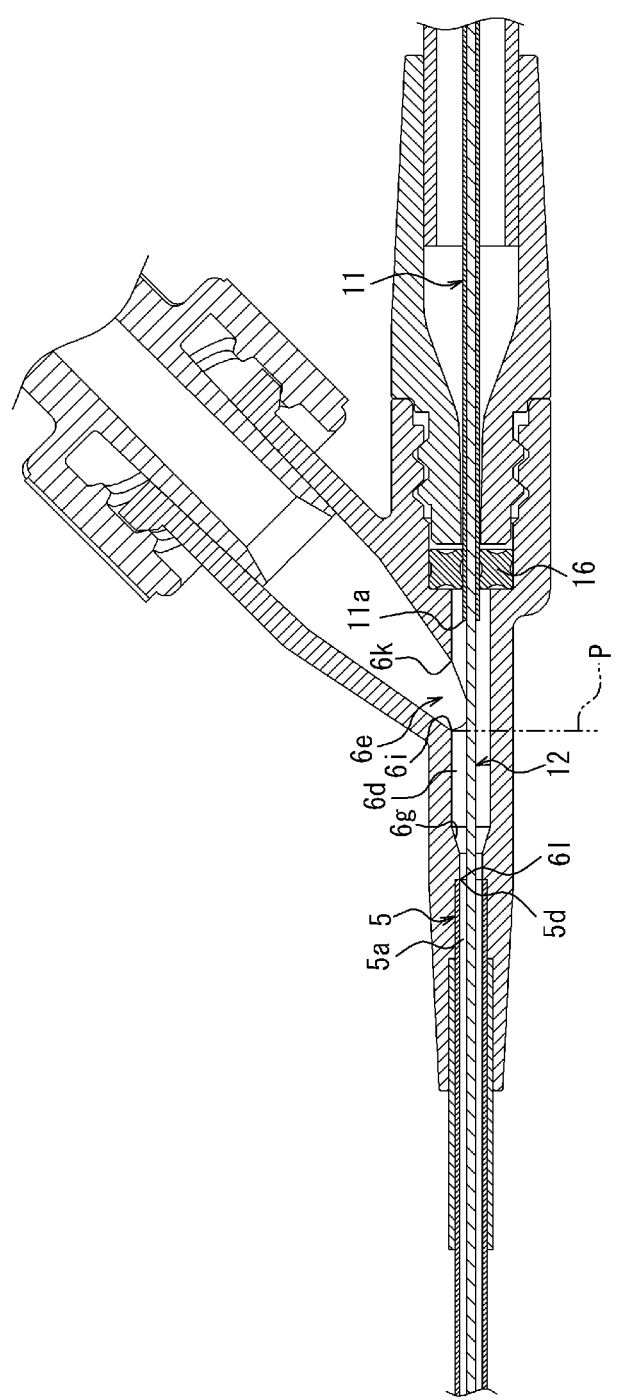
FIG. 6 is a cross-sectional view showing the peripheral portion of the relay connector in a state where the drive shaft and the support tube are in the backward limit position.

As shown in FIG. 6, the distal end 11a of the support tube 11 can be moved to a position behind or proximal to the front end (distal edge) 6i of the communication port 6e. That is, the distal end 11a of the support tube 11 can be moved to a position behind the position P. More specifically, the distal end 11a of the support tube 11 is located behind the front end 6i of the communication port 6e in the backward limit position (expansion limit state of the telescope portion 14). Therefore, by performing the priming processing in a state where the distal end 11a of the support tube 11 is moved to the position behind the position P, a flow path resistance of priming liquid flowing into the main lumen 6d from the communication port 6e can be reduced, and the priming processing can be smoothly performed. In the priming processing, the priming liquid sequentially fills the injection lumen 6f, the main lumen 6d, and the lumen 5a, and flows until being discharged from the discharge port provided at the distal end of the lumen 5a. Therefore, air inside the injection lumen 6f, the main lumen 6d, and the lumen 5a is discharged from the discharge port.

More specifically, the distal end 11a of the support tube 11 can be moved to a position behind or proximal of a rear end (proximal end) 6k of the communication port 6e. That is, as shown in FIG. 6, the distal end 11a of the support tube 11 is located behind the rear end 6k of the communication port 6e at the backward limit position.

The distal end 11a of the support tube 11 may be movable to the position behind (proximal of) the front end 6i of the communication port 6e, but in order to further reduce the flow path resistance, it is preferable that the distal end 11a is movable to a position behind a center of the communication port 6e (located behind or proximal to the center of the communication port 6e in the backward limit position), and it is more preferable that the distal end 11a is movable to a position behind or proximal to the rear end 6k of the communication port 6e (located behind the rear end 6k of the communication port 6e in the backward limit position).

As shown in FIG. 6, the distal end 11a of the support tube 11 is located in front of the sealing member 16 in the backward limit position. That is, in the backward limit position of the drive shaft 12 and the support tube 11, the distal end 11a of the support tube 11 is located proximal of the rear end 6k of the communication port 6e and distal of the sealing member 16.

When the drive shaft 12 and the support tube 11 are moved forward to the forward limit position after the priming processing, the diameter-reduced portion 6g can smoothly guide the distal end 11a of the support tube 11 to the distal end 6l of the main lumen 6d, and the distal end 6l of the main lumen 6d, which is flush with the base end 5d of the lumen 5a, can further smoothly guide the distal end 11a of the support tube 11 to the inside of the lumen 5a.

The relay connector 6 (the first member 18 and the second member 19), the support tube 11, and the sheath 5 are preferably made of a synthetic resin, but are not limited thereto.

The detailed description above describes an embodiment of a diagnostic imaging catheter and a diagnostic imaging apparatus representing an example of the inventive diagnostic imaging catheter and diagnostic imaging apparatus disclosed here. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A diagnostic imaging catheter, comprising:
    an axially extending drive shaft that includes a distal end portion, and a signal transmitter and receiver at the distal end portion of the drive shaft, the drive shaft and the signal transmitter and receiver being rotatable together and being movable together axially forward and backward;
    a support tube provided on an outer periphery of the drive shaft and extending in an axial direction along a part of an axial extent of the drive shaft, the support tube being configured to move axially forward and backward together with the drive shaft, the support tube including a distal-most end;
    a sheath in which the drive shaft is positioned, the sheath including a proximal end;
    a relay connector connected to the proximal end of the sheath;
    a sealing member positioned to provide a seal between the relay connector and the support tube at a position proximal of the proximal end of the sheath;
    the relay connector being divided into a main lumen that extends from the sealing member to the proximal end of the sheath and an injection lumen into which is injectable a priming liquid, the injection lumen communicating with the main lumen at a communication port so that the priming liquid injected into the injection port flows into the main lumen by way of the communication port, the communication port including a distal edge; and
    the support tube being axially movable so that the distal-most end of the support tube is positionable axially between the sealing member and the distal edge of the communication port.

2. The diagnostic imaging catheter according to claim 1, wherein the support tube is axially movable so that the distal-most end of the support tube is positionable distal of the distal edge of the communication port.

3. The diagnostic imaging catheter according to claim 2, wherein the distal-most end of the support tube is located distal of the distal edge of the communication port at an end of a pullback operation by an external device.

4. The diagnostic imaging catheter according to claim 1, wherein the sheath incudes a lumen in which the drive shaft is positioned, the lumen in the sheath including a proximal end, a distal end of the main lumen of the relay connector being located at the proximal end of the lumen in the sheath.

5. The diagnostic imaging catheter according to claim 1, wherein the main lumen in the relay connector includes a distal portion possessing an inner diameter that gradually decreases in a direction towards the proximal end of the sheath.

6. The diagnostic imaging catheter according to claim 1, wherein the communication port is positioned intermediate the sealing member and the proximal end of the sheath.

7. The diagnostic imaging catheter according to claim 1, wherein the injection lumen includes a central axis that intersects the main lumen of the relay connector at a position intermediate the sealing member and the proximal end of the sheath.

8. The diagnostic imaging catheter according to claim 1, wherein the sheath incudes a lumen in which the drive shaft is positioned, the lumen in the sheath being in fluid communication with the main lumen in the relay connector so that the priming liquid injected into the injection lumen and introduced into the main lumen by way of the communication port flows into the lumen in the sheath.

9. The diagnostic imaging catheter according to claim 1, wherein the support tube is axially movable so that the distal-most end of the support tube is positionable proximal of a proximal edge of the communication port.

10. A diagnostic imaging apparatus, comprising:
    a diagnostic imaging catheter; and
    an external device connectable to the diagnostic imaging catheter;
    the diagnostic imaging catheter comprising:
        an axially extending drive shaft that includes a distal end portion, and a signal transmitter and receiver at the distal end portion of the drive shaft, the drive shaft and the signal transmitter and receiver being rotatable together and being movable together axially forward and backward;
a support tube provided on an outer periphery of the drive shaft and extending in an axial direction along a part of an axial extent of the drive shaft, the support tube being configured to move axially forward and backward together with the drive shaft, the support tube including a distal-most end;
a sheath in which the drive shaft is positioned, the sheath including a proximal end;
a relay connector connected to the proximal end of the sheath;
a sealing member positioned to provide a seal between the relay connector and the support tube at a position proximal of the proximal end of the sheath;
the relay connector being divided into a main lumen that extends from the sealing member to the proximal end of the sheath and an injection lumen into which is injectable a priming liquid, the injection lumen communicating with the main lumen at a communication port so that the priming liquid injected into the injection port flows into the main lumen by way of the communication port, the communication port including a distal edge;
the support tube being axially movable so that the distal-most end of the support tube is positionable axially between the sealing member and the distal edge of the communication port; and
the external device including a limiting portion that limits axial backward movement of the distal-most end of the support tube of the diagnostic imaging catheter when the diagnostic imaging catheter is connected to the external device and the external device is performing a pullback operation of the drive shaft so that the distal-most end of the support tube does not move proximally beyond the distal edge of the communication port.

11. The diagnostic imaging apparatus according to claim 10, wherein the support tube is axially movable so that the distal-most end of the support tube is positionable distal of the distal edge of the communication port.

12. The diagnostic imaging apparatus according to claim 10, wherein the sheath incudes a lumen in which the drive shaft is positioned, the lumen in the sheath including a proximal end, a distal end of the main lumen of the relay connector being located at the proximal end of the lumen in the sheath.

13. The diagnostic imaging apparatus according to claim 10, wherein the main lumen in the relay connector includes a distal portion possessing an inner diameter that gradually decreases in a direction towards the proximal end of the sheath.

14. The diagnostic imaging apparatus according to claim 10, wherein the communication port is positioned intermediate the sealing member and the proximal end of the sheath.

15. The diagnostic imaging apparatus according to claim 10, wherein the injection lumen includes a central axis that intersects the main lumen of the relay connector at a position intermediate the sealing member and the proximal end of the sheath.

16. The diagnostic imaging apparatus according to claim 10, wherein the sheath incudes a lumen in which the drive shaft is positioned, the lumen in the sheath being in fluid communication with the main lumen in the relay connector so that the priming liquid injected into the injection lumen and introduced into the main lumen by way of the communication port flows into the lumen in the sheath.

17. The diagnostic imaging apparatus according to claim 10, wherein the support tube is axially movable so that the distal-most end of the support tube is positionable proximal of a proximal edge of the communication port.

18. A diagnostic imaging catheter, comprising:
an axially extending drive shaft that includes a distal end portion, and a signal transmitter and receiver at the distal end portion of the drive shaft, the drive shaft and the signal transmitter and receiver being rotatable together and being movable together axially forward and backward;
a support tube provided on an outer periphery of the drive shaft and extending in an axial direction along a part of an axial extent of the drive shaft, the support tube being configured to move axially forward and backward together with the drive shaft, the support tube including a distal-most end;
a sheath in which the drive shaft is positioned, the sheath including a proximal end;
a relay connector connected to the proximal end of the sheath;
a sealing member positioned to provide a seal between the relay connector and the support tube, the sealing member being located on a proximal side of the proximal end of the sheath so that the proximal end of the sheath is on a distal side of the sealing member;
the relay connector being divided into a main lumen that extends from the sealing member to the proximal end of the sheath and an injection lumen into which is injectable a priming liquid, the injection lumen communicating with the main lumen at a communication port so that the priming liquid injected into the injection port flows into the main lumen by way of the communication port, the communication port including a distal edge; and
the support tube being axially movable between one position in which the distal-most end of the support tube is positioned on the distal side of the distal edge of the communication port and another position in which the distal-most end of the support tube is positioned on the proximal side of the distal edge of the communication port.

* * * * *